(12) United States Patent
Hasegawa et al.

(10) Patent No.: US 7,915,453 B2
(45) Date of Patent: Mar. 29, 2011

(54) PROCESS FOR PRODUCING TERTIARY AMINE

(75) Inventors: Shoji Hasegawa, Wakayama (JP); Toru Nishimura, Wakayama (JP); Atsushi Hirota, Wakayama (JP)

(73) Assignee: Kao Corporation, Tokyo (JP)

( * ) Notice: Subject to any disclaimer, the term of this patent is extended or adjusted under 35 U.S.C. 154(b) by 372 days.

(21) Appl. No.: 12/159,094

(22) PCT Filed: Dec. 26, 2006

(86) PCT No.: PCT/JP2006/326331
§ 371 (c)(1),
(2), (4) Date: Jun. 25, 2008

(87) PCT Pub. No.: WO2007/074922
PCT Pub. Date: Jul. 5, 2007

(65) Prior Publication Data
US 2010/0298608 A1    Nov. 25, 2010

(30) Foreign Application Priority Data
Dec. 28, 2005   (JP) ............................. 2005-379876

(51) Int. Cl.
*C07C 209/26*   (2006.01)
(52) U.S. Cl. ............................................. 564/489
(58) Field of Classification Search ............ 564/489
See application file for complete search history.

(56) References Cited

U.S. PATENT DOCUMENTS

| | | | |
|---|---|---|---|
| 2,746,993 | A | 5/1956 | Dean |
| 4,625,063 | A | 11/1986 | Yokota et al. |
| 7,402,702 | B2 | 7/2008 | Oguri et al. |
| 2008/0004472 | A1 | 1/2008 | Nishimura et al. |

FOREIGN PATENT DOCUMENTS

| | | |
|---|---|---|
| EP | 0 394 968 | 10/1990 |
| EP | 1 604 739 | 12/2005 |
| JP | 3 4534 | 1/1991 |
| JP | 3 68541 | 3/1991 |

OTHER PUBLICATIONS

Kimura et al., Catalysis Letters (2005), 99(3-4), p. 119-131.*
Baiker, Alfons et al., "Catalytic Synthesis of Higher Aliphatic Amines from the Corresponding Alcohols", Catal. Rev. Sci. Eng., vol. 27, No. 4, pp. 653-697, (1985).
"Shin Jikken Kagaku Koza 14 Yuki Kagobutsu No Gosei to Hanno III" (New Experimental Chemistry Course 14, Organic Compound Synthesis and Reaction III), pp. 1410-1423 (1978).
"Shin Jikken Kagaku Koza 14 yuki Kagobutsu No Gosei to Hanno III" (New Experimental Chemistry Course 14, Organic Compound Synthesis and Reaction III), Published by Maruzen Co., Ltd., pp. 1340-1341, (1978).
Pitacco, Giuliana et al., "Oxidation and reduction of enamines", The Chemistry of Enamines, Published by John Wiley and Sons Ltd., Chapter 17, No. III, pp. 922-923, 960-961 and 974-981, (1994).
U.S. Appl. No. 11/911,032, filed Oct. 9, 2007, Nishimura et al.

* cited by examiner

*Primary Examiner* — Brian J Davis
(74) *Attorney, Agent, or Firm* — Oblon, Spivak, McClelland, Maier & Neustadt, L.L.P.

(57) ABSTRACT

Disclosed is a process for producing a tertiary amine from a primary or secondary amine and alcohol as corresponding starting materials, which includes step (i) of dehydrogenating an alcohol to obtain an aldehyde, step (ii) of reacting the aldehyde with a primary or secondary amine to obtain a primary or secondary amine adduct, and step (iii) of hydrogenating the primary or secondary amine adduct to obtain a tertiary amine, wherein step (ii) is carried out independently of the other steps.

19 Claims, 2 Drawing Sheets

PROCESS FOR PRODUCING TERTIARY AMINE

FIELD OF THE INVENTION

The present invention relates to a process for producing a tertiary amine from its corresponding primary or secondary amine and an alcohol as the starting materials.

BACKGROUND OF THE INVENTION

Fatty amines produced from tallow, coconut oil, palm oil etc. as the starting material are important intermediates in household and industrial fields. Particularly, fatty tertiary amines are converted into quaternary ammonium salts etc. and utilized in a wide variety of applications such as the field of fiber softening finishers, antistatic agents, rinse bases etc.

Conventionally, a method of producing a tertiary amine from an alcohol and a primary or secondary amine as the starting materials is well-known, but the corresponding tertiary amine is hardly obtained highly selectively. For example, JP-B 3-4534 discloses a method of obtaining an objective tertiary amine in high yield by using a catalyst based on copper/nickel/third component. However, even if this catalyst is used, considerable undesired side products are generated when the amount of the catalyst is increased or the reaction temperature is raised for improving manufacturing ability in converting an alcohol into the corresponding tertiary amine in the same reaction system.

Such side products include those generated by the reaction in which a primary or secondary amine as the starting material undergoing disproportionation reaction depending on the action of a catalyst and high-temperature conditions is involved. The reaction of converting a primary or secondary amine into the corresponding tertiary amine is competitive to the disproportionation reaction of a primary or secondary amine, and when a primary or secondary amine is reacted with an alcohol in the same reaction system in the presence of a catalyst at high temperatures in order to obtain the corresponding tertiary amine, generation of the above side products is inevitable in principle.

It has been reported that the reaction of converting an alcohol and a primary or secondary amine into the corresponding tertiary amine proceeds via a plurality of elementary steps. For example, Baiker et al. (Catal. Rev. Sci. Eng., 27(4), 653 (1985)) has confirmed the presence of, as reaction intermediates, an aldehyde generated by dehydrogenation of an alcohol, an imine and/or an enamine generated by adding a primary or secondary amine to the aldehyde and subsequent dehydration thereof. Techniques for carrying out these elementary steps individually and separately are well-known. The step of dehydrogenating an alcohol is disclosed in for example U.S. Pat. No. 2,746,993, the step of adding a primary or secondary amine to an aldehyde is disclosed in for example "Shin Jikken Kagaku Koza 14 Yuki Kagobutsu No Gosei To Hanno III" (New Experimental Chemistry Course 14, Organic Compound Synthesis and Reaction III), p. 1410 and p. 1422, published by Maruzen Co., Ltd. (1978), and the step of hydrogenating an imine and enamine to generate the corresponding secondary or tertiary amine is disclosed in for example "Shin Jikken Kagaku Koza 14 Yuki Kagobutsu No Gosei To Hanno III" (New Experimental Chemistry Course 14, Organic Compound Synthesis and Reaction III), p. 1340, published by Maruzen Co., Ltd. (1978) and The chemistry of enamines, Ch. 17, III, published by John Wiley & Sons Ltd. (1994).

A method wherein a carbonyl group-containing compound or a compound capable of forming a carbonyl group under reducing amination conditions is converted, through reducing amination, into an aminated compound is disclosed in JP-A 3-68541. It is described therein that in a liquid solvent, (a) a carbonyl group-containing compound is contacted with a primary or secondary amine under imine-forming conditions, to form an imino or enamino group-containing compound and then (b) the imino or enamino group-containing compound is contacted with hydrogen under amine-forming conditions to form an amine product, whereby the formation of a hydroxyl group by hydrogenating the carbonyl group can be minimized in the process.

SUMMARY OF THE INVENTION

The present invention provides a process for producing a tertiary amine from a primary or secondary amine and an alcohol as corresponding starting materials, which includes:
 step (i) of dehydrogenating an alcohol to obtain an aldehyde,
 step (ii) of reacting the aldehyde with a primary or secondary amine to obtain a primary or secondary amine adduct, and
 step (iii) of hydrogenating the primary or secondary amine adduct to obtain a tertiary amine,
 wherein step (ii) is carried out independently of the other steps.

DETAILED DESCRIPTION OF THE INVENTION

In the above shown elementary steps, carried out individually, there is no example of techniques consisting of a combination of the individual techniques described above to convert an alcohol and a primary or secondary amine into the corresponding tertiary amine.

In JP-A 3-68541, the ratio at which a hydroxyl group is formed can be lowered, but a specific means of preventing the disproportionation reaction of a primary or secondary amine is not explicitly stated therein, and a method of preventing formation of side products generated as a result of such disproportionation reaction is not suggested therein. It is not reasonable that under the conditions where dehydrogenation of a hydroxyl group is difficult, an alcohol as a compound capable of forming a carbonyl group is used as the starting material, and use of an alcohol and a primary or secondary amine as the starting materials in this method does not enable production of the corresponding tertiary amine in high yield.

The present invention provides a process for producing a tertiary amine highly selectively at a high yield from a corresponding primary or secondary amine and an alcohol as the starting materials.

The present inventors have found that, when an alcohol and a primary or secondary amine are used as the starting materials to produce the corresponding tertiary amine, a step of reacting an aldehyde generated by dehydrogenation of an alcohol with a primary or secondary amine to obtain a primary or secondary amine adduct, is carried out independently to produce a corresponding tertiary amine at a high selectivity at a high yield.

According to the process of the present invention, the objective tertiary amine can be obtained highly selectively in high yield. Particularly by carrying out a cycle consisting of the step (i) to step (iii) repeatedly, the degree of conversion into the objective tertiary amine can be increased while high selectivity is maintained.

The alcohol used as a starting material in the present invention is preferably a linear or branched C8 to C36 saturated or unsaturated aliphatic alcohol. Specific examples include octyl alcohol, lauryl alcohol, myristyl alcohol, stearyl alcohol, behenyl alcohol and oleyl alcohol, a mixed alcohol thereof, Ziegler alcohol obtained by the Ziegler process, an oxo alcohol obtained by an oxo process, and Guerbet alcohol.

The primary or secondary amine used as a starting material in the present invention is preferably an aliphatic primary or secondary amine, and examples thereof include methylamine, dimethylamine, ethylamine, diethylamine, dodecylamine, didodecylamine etc., more preferably a monoalkylamine or dialkylamine having a C1 to C4 alkyl group, even more preferably a monoalkylamine or dialkylamine having a C1 to C2 alkyl group, even more preferably dimethylamine or monomethylamine.

A tertiary amine, produced from an alcohol and a primary or secondary amine as corresponding starting materials, has an alkyl group and/or an alkenyl group, derived from the alcohol, which group is substituted for a hydrogen atom bound to the nitrogen atom of the primary or secondary amine. For example, the tertiary amine obtained from lauryl alcohol and dimethylamine is N-dodecyl-N,N-dimethylamine which is distinguished from tertiary amine side products N,N-didodecyl-N-methylamine and N,N,N-tridodecylamine formed by reaction of ammonia and methylamine generated by disproportionation of dimethylamine.

In the present invention, the reaction of an alcohol and a primary or secondary amine as the starting materials includes step (i), step (ii) and step (iii). The reaction systems for carrying out step (i) to step (iii) may be in a tank form, a tubular form or another preferable form, and the reaction system at least in step (ii) is clearly distinguished from the reaction systems in the other steps, and a mixture of the reactants (starting materials and/or intermediates) and/or the product (formed tertiary amine) is transferred substantially continuously therebetween, whereby the reactions in the respective steps proceed sequentially.

By carrying out step (i), step (ii) and step (iii) in this order, the starting alcohol is dehydrogenated in step (i) to form the corresponding aldehyde, and this aldehyde is reacted with a primary or secondary amine in step (ii) to form the corresponding adduct, and this adduct is hydrogenated in step (iii) to obtain the objective tertiary amine.

When the aldehyde and/or the primary or secondary amine adduct, formed in reactions of the steps, respectively, does not exhibit a high stability under the reaction conditions, generation of large amounts of the intermediates in the steps facilitates condensation etc. of the intermediates to increase side products readily. In this case, the reaction in each step is suppressed so as not to form these intermediates in a too large amount, while the cycle consisting of the step (i) to step (iii) is repeatedly carried out, whereby the degree of conversion into the objective tertiary amine can be increased while high selectivity is maintained.

When the materials are circulated in the cycle consisting of step (i) to step (iii), the order of continuously transferring a mixture of the reactants (starting materials and/or intermediates) and/or the product (formed tertiary amine) between the steps is not particularly limited insofar as the reaction in each step is not inhibited. For example, the materials may be circulated twice or more in the cycle consisting of step (i)/step (ii)/step (iii), or twice or more in the cycle of step (i) and step (ii), and simultaneously or separately in the cycle of step (ii) and step (iii). The materials may be circulated twice or more among the reaction systems in the step (iii) and step (i) (a primary or secondary amine adduct is hydrogenated while an alcohol is dehydrogenated) and the reaction system in step (ii). A method of circulating the materials in the cycle of step (i) and step (ii) and simultaneously in the cycle of step (ii) and step (iii) is sometimes preferable because the flow rate and other conditions in step (i) and step (iii) can be independently regulated by carrying step (ii) in a buffer tank.

When a mixture of the reactants (starting materials and/or intermediates) and/or the product (formed tertiary amine) is maintained unnecessarily without subjecting them to any step where an aldehyde and/or a primary or secondary amine adduct does not exhibit high stability, their condensation is facilitated and side products are increased. Accordingly, the time required for transferring a mixture containing them from one step to another step is preferably as short as possible. When an intermediate tank or a tank tube needing a certain retention time is arranged for the purpose of gas/liquid or solid/liquid separation between the steps or of heat exchange for temperature regulation, the retention time therein is preferably as short as possible.

The method of feeding a mixture of the reactants (starting materials and/or intermediates) and/or the product (formed tertiary amine) in step (i) to step (iii) may be a batch or continuous method. Similarly, the method of recovering the mixtures in each step may be arbitrarily selected from batch and continuous methods.

Step (i) is a step of dehydrogenating an alcohol to obtain the corresponding aldehyde. For example, when lauryl alcohol is used as the alcohol, the aldehyde obtained in this step is dodecyl aldehyde.

The method of dehydrogenation in step (i) is not particularly limited and can be carried out according to known techniques, and a method of using a dehydrogenation catalyst is advantageous from an industrial point of view. As the dehydrogenation catalyst, a catalyst on which a metal such as Cu or the like is supported, usually applied to dehydrogenation, may be preferably used. Such catalysts include, for example, those wherein Cu alone, or 2 or 3 more metals, that is, Cu plus transition metal elements such as Cr, Co, Ni, Fe and Mn, are supported on supports such as silica, alumina, titania and zeolite. The shape of the catalyst is not particularly limited, but when the catalyst is produced in the form of granules such as pellets, noodles, tablets etc. or as a molded catalyst with a structure such as open-cell foam, honeycomb etc. or as a film-type catalyst having the catalyst fixed on the surface of a support, continuous supply of the reactants and/or continuous recovery of the product can be preferably facilitated by a fixed-bed reactor loaded with the catalyst or a reactor including a fixed-bed catalyst. A wetted wall tower fixed-bed reactor by a reactor wall surface-modified catalyst can also be preferably used for the same reason. The method of feeding a mixture of the reactants (starting materials and/or intermediates) and/or the product (formed tertiary amine) to the fixed-bed reactor and/or the method of feeding the gas may be carried out with any of upflow, downflow and side flow.

In step (i), the reactants may be present in the gaseous phase or in the liquid phase. When a metal catalyst is used, an oxidizing atmosphere such as oxygen and air can also be used for active dehydrogenation by oxidation reaction, but the reaction in a nonoxidative atmosphere is advantageous for maintaining the reduced state of the catalyst. The atmosphere may be hydrogen or an atmosphere other than hydrogen to promote dehydrogenation reaction, and for example, a nitrogen or rare gas atmosphere can be mentioned. For the purpose of suppressing the reverse reaction of adding hydrogen again to the aldehyde, the pressure in the system is desirably not significantly higher than normal pressures. The temperature in step (i) is preferably 50 to 300° C., more preferably 100 to 250° C.

Step (ii) is a step of reacting an aldehyde with a primary or secondary amine to obtain the corresponding adduct. For example, when the aldehyde is dodecyl aldehyde generated by dehydrogenation of lauryl alcohol and the primary or secondary amine is dimethylamine, the adduct obtained by this process is 1-(N,N-dimethylamino)-1-dodecanol and/or its dehydrated enamine i.e. 1-(N,N-dimethylamino)-1-dodecene. The reaction of converting an aldehyde and a primary or secondary amine into the corresponding adduct proceeds even under more moderate conditions than the conditions required in the other steps.

Step (ii) is independent of the other steps. Step (ii) is conducted preferably under moderate conditions. As described above, when a primary or secondary amine is reacted with an alcohol in the same reaction system in the presence of a catalyst at high temperatures in order to obtain the corresponding tertiary amine, the primary or secondary amine undergoing disproportionation reaction due to the action of a catalyst and high-temperature conditions is reacted with the starting alcohol, thereby generating side products inevitably in principle. Step (ii) is made independent of the other steps and carried out under moderate conditions to prevent the disproportionation reaction of a primary or secondary amine and obtain a tertiary amine from an alcohol and a primary or secondary amine correspondingly at a very high yield. By carrying out the reaction under moderate conditions, side reactions such as condensation of aldehydes or primary or secondary amine adducts in step (ii) can also be prevented.

As a method of realizing the moderate conditions in step (ii), there is a method of carrying out step (ii) in the absence of a catalyst. Some catalysts which can be preferably used in step (i) and/or step (iii) promote the disproportionation reaction of a primary or secondary amine, and by carrying step (ii) in the absence of such catalysts, the disproportionation reaction of the primary or secondary amine can be suppressed. It is preferable that step (ii) is made independent of the other steps and carried out under the conditions where a part and/or the whole of the catalyst used in step (i) and/or step (iii) is not fed to step (ii) as mixed in a mixture of the reactants (starting materials and/or intermediates) and/or the product (formed tertiary amine).

In another method of realizing the moderate conditions in step (ii), the temperature is made lower than in step (i) and step (iii). Specifically, there is a method of carrying step (ii) at a temperature of 170° C. or less. The disproportionation reaction of the primary or secondary amine may be accelerated by temperature, and thus step (ii) is carried out under such low temperature condition as not to solidify the reactants, whereby the disproportion reaction of the primary or secondary amine can be suppressed.

When the catalyst is not present, the temperature condition in step (ii) is preferably 250° C. or less, more preferably 170° C. or less, even more preferably 150° C. or less, further more preferably 120° C. or less, in order to suppress side reactions such as the disproportionation reaction of a primary or secondary amine, the condensation of aldehydes or primary or secondary amine adducts, etc. When the catalyst is present, the temperature is preferably 150° C. or less, more preferably 120° C. or less, even more preferably 100° C. or less. The lower limit is not particularly limited and may be in such a range that the reactants are not solidified, and usually the temperature is preferably 20° C. or more, more preferably 25° C. or more, even more preferably 30° C. or more.

The method of reacting an aldehyde with a primary or secondary amine in step (ii) can be carried out according to known techniques and is not particularly limited insofar as the conditions described above are satisfied.

The reactor used in step (ii) may be in an arbitrary form such as a tank form or a tubular form, and it is preferably to use forms such as a complete-stirred tank, a packed tower and a bubble tower in order to facilitate continuous supply of the reactants and/or continuous recovery of the product. In the case of a tubular reactor, for example, the method of feeding a mixture of the reactants (starting materials and/or intermediates) and/or the product (formed tertiary amine) and/or the method of feeding the gas may be carried out with any of upflow, downflow and side flow.

Preferably, the pressure in step (ii) is not significantly lower than normal pressures in order that the aldehyde and the primary or secondary amine are present in a condensed phase to accelerate the reaction. However, the reaction is carried out preferably under reduced pressure to remove water generated by dehydration from the system in order that the reverse reaction of generating the aldehyde and the primary or secondary amine is suppressed by promoting the dehydration reaction of the adduct to form an imine and/or an enamine. Which condition is used can be determined by consideration of the physical properties of the aldehyde, the primary or secondary amine and the corresponding adduct in comparison with water. For example, when dodecyl aldehyde is reacted with dimethylamine, the reaction is conducted desirably under reaction conditions at normal pressures or so.

For carrying out step (ii) effectively by accelerating the dissolution of the primary or secondary amine into the liquid phase when the primary or secondary amine is present in the gaseous phase, it is preferable that a gas component such as hydrogen and/or an inert gas for example contained in a mixture of the reactants (starting materials and/or intermediates) to be subjected to step (ii) and/or the product (formed tertiary amine) and/or a gas component fed in step (1) or generated in step (i) is separated prior to step (ii) from a mixture of the reactants (starting materials and/or intermediates) and/or the product (formed tertiary amine). Further, the unreacted primary or secondary amine remaining in a mixture of the reactants (starting materials and/or intermediates) in step (ii) and/or the product (formed tertiary amine) is preferably separated and removed after step (ii) thereby preventing it from being brought into the steps other than step (ii). This procedure of separation and removal after step (ii) includes, for example, a method of separating the primary or secondary amine present in the gaseous phase by gas/liquid separation, and in this case, a procedure of bubbling the liquid with an inert gas such as nitrogen or a procedure of separation and removal under reduced pressure is preferable for higher efficiency.

Step (iii) is a step of hydrogenating the primary or secondary amine adduct generated in step (ii) to obtain the corresponding tertiary amine. For example, when the primary or secondary amine adduct is 1-(N,N-dimethylamino)-1-dodecanol and/or its dehydrated enamine i.e. 1-(N,N-dimethylamino)-1-dodecene, the corresponding tertiary amine is N-dodecyl-N,N-dimethylamine.

The method of hydrogenation in step (iii) is not particularly limited and can be carried out according to known techniques, and a method of using a dehydrogenation catalyst in a hydrogen atmosphere is advantageous from an industrial point of view. Such catalysts include those wherein Cu or Ni alone or 2 or 3 or more metal components of Cu and/or Ni and additionally a transition metal element (s) such as Cr, Co, Ni, Fe or Mn, are supported on supports such as silica, alumina, titania and zeolite, or catalysts consisting of a noble metal transition element alone such as Pt or a composite thereof with carbon. Among catalysts preferably used as the dehydrogenation catalyst in step (i), there are catalysts which can also be preferably used as the hydrogenation catalyst in step (iii), and the catalyst used in step (iii) may be the same as in step (i). The shape of the catalyst is not particularly limited, but when the catalyst is produced in the form of granules such as pellets, noodles, tablets etc. or as a molded catalyst with a structure such as open-cell foam, honeycomb etc. or as a film-type catalyst having the catalyst fixed on the surface of a support, continuous supply of the reactants and/or continuous recovery of the product can be preferably facilitated by a fixed-bed reactor loaded with the catalyst. A wetted wall tower fixed-bed reactor by a reactor wall surface-modified catalyst can also be preferably used for the same reason. The method of feeding a mixture of the reactants (starting materials and/or intermediates) to the fixed-bed reactor and/or the product (formed tertiary amine) and/or the method of feeding the gas may be carried out with any of upflow, downflow and side flow.

In step (iii), the reactants may be present in the gaseous phase or the liquid phase. For promoting the hydrogenation reaction, the partial pressure of hydrogen is preferably higher in the atmosphere, and thus the pressure in the system is desirably not significantly lower than normal pressures. The temperature in step (iii) is not particularly limited, but is preferably 50 to 300° C., more preferably 100 to 250° C.

The film-type catalyst used in the present invention described in step (i) and step (iii) is different from a conventional packed-bed catalyst irregular in shape having several millimeters or thereabout, and refers to a catalyst in the form of a thin film having a thickness of 500 µm or less. The process of transferring the reactants and the product in the inside of the catalyst is governed by diffusion, and the distance is reduced to 500 µm or less, whereby the material transfer between the inside and outside of the catalyst can be promoted thereby effectively utilizing the whole of the catalyst and simultaneously suppressing the excessive reaction of the intermediate reaction product in the inside of the catalyst. The thickness of the film-type catalyst is particularly preferably 100 µm or less, more preferably 50 µm or less, in order to significantly increase the reaction activity per catalyst unit weight. The lower limit of the thickness is preferably 0.01 µm or more, even more preferably 1 µm or more, in order to secure the strength of the catalyst layer and attain durability of the strength thereof.

The structure of the film-type catalyst includes various structures depending on the shape of a reactor. For example, a catalyst coating layer formed on a wall in a tube, a catalyst formed in a tube in the form of a thin plate by which the tube is divided in an axial direction into a plurality of flow paths, etc. are mentioned and can be used preferably in a tubular circulating reactor. The surface of the catalyst where supply of the reactants to the catalyst and recovery of the product from the catalyst occur is desirably as large as possible for efficient progress of the reaction. For achieving the above requirement, it is preferable to use the film-shaped catalyst arranged in a structure consisting of assembled tubes each having an inner diameter of several millimeters to several centimeters or in the inner wall of a honeycomb structure having several ten to several hundred cells per square inch.

For forming the film-type catalyst in the various structures described above, there is for example a method of forming the catalyst active substance itself into a honeycomb structure, but from the viewpoint of satisfying both a thin catalyst layer and high mechanical strength, the film-type catalyst is preferably fixed on the surface of a support. The film-type catalyst support is preferably a metal foil. There is for example a method wherein a coating layer containing the catalyst active substance is formed on the surface of a metallic or other rigid, tubular, planar or honeycomb support to produce the film-type catalyst. As the coating method, it is possible to use conventionally known methods including not only physical deposition such as spattering, chemical deposition, and impregnation from a solution, but also various coating methods with a binder, such as blade coating, spray coating, dip coating, spin coating, gravure coating and die coating.

The film-type catalyst can contain a binder which does not act as an active substance but fixes the active substance to form the film-type catalyst. The binder includes high-molecular or inorganic compounds which are durable to the reaction environment, do not adversely affect the reaction system and have not only a property of binding particles of the active substance together or binding the active substance to the surface of a support but also properties such as chemical resistance and heat resistance. Examples of the binder include cellulose resin such as carboxymethyl cellulose and hydroxyethyl cellulose, fluorine-based resin such as polyethylene tetrafluoride and polyvinylidene fluoride, high-molecular compounds such as urethane resin, epoxy resin, polyester resin, phenol resin, melamine resin, silicone resin, polyvinyl alcohol, polyimide resin and polyimide amide resin, and inorganic compound sol such as silica and alumina.

The internal structure of the film-type catalyst depends significantly on the type of the active substance constituting the catalyst and on the method of preparing the catalyst, and may form a dense continuous phase or may be porous. For example, when the catalyst is a thin film formed on the surface of a support by sputtering and chemical vapor deposition, the catalyst can have a dense continuous phase, while when the powdery active substance is formed on the surface of a support by wet or dry coating, the catalyst can be porous.

As the method of producing the film-type catalyst, it is particularly preferable to use a method of forming, on a support, a coating containing a powdery catalyst active substance and a binder for fixing it. Particularly, in the film-type catalyst obtained by forming, on a support, a coating containing a powdery catalyst together with synthetic resin used as a binder and in the method of producing the same, the compounding ratio of the powdery catalyst to the synthetic resin can be regulated in such a suitable range as to control the degree of exposure of the powdery catalyst and the binding strength among the catalyst powders and the binding strength between the support and the catalyst powders.

In the film making method, the compounding ratio is preferably a ratio of 20 to 80 parts by mass of the synthetic resin to 100 parts by mass of the powdery catalyst. The film-type catalyst exhibiting the reaction activity particularly effective as a film-type catalyst and hardly releasing its coating can be obtained by further controlling the pore volume per unit area of the support in the range of 0.5 to 30 mL/m$^2$.

In the internal structure of the film-type catalyst obtained by the above film making method, the surface of the powdery catalyst is coated wholly or partially with the synthetic resin, and the powdery catalyst particles are bound to one another via the synthetic resin, and a large number of the powdery catalyst particles are deposited in the direction of thickness. A large number of such deposited powdery catalyst particles form a 3-dimensional network structure via the synthetic resin, and air layers lie scattered in gaps among the powdery catalyst particles, and preferably the synthetic resin itself also has a pore structure. The film-type catalyst can have a slanting structure wherein the ratio of the powdery catalyst to the synthetic resin is changed in the direction of thickness, or the film-type catalyst layer may consist of two or more catalyst layers different in the ratio of the powdery catalyst to the synthetic resin therein or consist of two or more catalyst layers different in pore structure.

In the film-type catalyst obtained by the film making method described above, the synthetic resin is contained preferably in an amount of 20 to 80 parts by mass relative to 100 parts by mass of the powdery catalyst, whereby the catalyst activity, or the binding strength among the powdery catalyst particles or between the powdery catalyst and the support, can be effectively exhibited. In the film-type catalyst, the pore volume of the catalyst layer per unit surface area of the support is desirably 0.5 to 30 mL/m$^2$, preferably 1 to 20 mL/m$^2$, more preferably 1 to 4 mL/m$^2$. When the pore volume is not less than 0.5 mL/m$^2$, the diffusion rate in the catalyst layer is increased, and upon application of the film-type catalyst to the reaction process, a high reaction rate can be obtained. When the pore volume is too large, the catalyst layer is made porous at high degree and the binding strength among the powdery catalyst particles and/or between the powdery catalyst and the support is reduced thus reducing the mechanical strength of the catalyst layer, while when the pore volume is not higher than 30 mL/m$^2$, the porosity of the catalyst layer becomes suitable, and the adhesion among the powdery catalyst particles and/or between the powdery catalyst and the support is increased. As a result, the mechanical strength of the catalyst layer is increased and simultaneously the material transfer of the reactants and product can be kept in an excellent state.

The pore structure of the film-type catalyst obtained by the film making method is determined in a step of eliminating volatile components and in a step of forming a twined structure of synthetic resin after coating a support with a coating containing the synthetic resin preferably in the range of 20 to 80 parts by mass relative to 100 parts by mass of the powdery catalyst. When the synthetic resin is thermosetting resin, the pore structure is determined at the time of forming a crosslinked structure (network structure) formed by progress of curing/crosslinking reaction, in addition to the step of eliminating volatile components. When the reaction is accompanied by condensation reaction, the pore structure is also influenced by the step of eliminating the condensation product. As a result of eager study, it was found that when the pore volume per unit surface area of the support, as an indicator characterizing the pore structure formed, is 0.5 to 30 mL/m$^2$, the sufficient reaction rate of the film-type catalyst in the reaction process and the retaining properties of the powdery catalyst can be preferably maintained.

The powdery catalyst, used in the film making method, is preferably a catalyst having properties meeting the suspension-bed process. In this case, the development time in the suspension bed process, as compared with the method of converting a catalyst active substance precursor fixed on a support into a catalyst active substance by treatment such as calcination, can be shortened because reaction characteristics in the reaction process can be secured. The production process can be simplified because a complicated production process for exhibiting the reaction activity, such as calcination treatment, is not necessary.

The powdery catalyst used in the film making method is preferably a powder having an average particle diameter of 0.01 to 500 preferably 0.1 to 100 μm, more preferably 0.5 to 50 μm, preferably with sharp distribution, and a specific surface area of 0.1 to 500 m$^2$/g, preferably 1 to 200 m$^2$/g, more preferably 10 to 100 m$^2$/g, as determined by the BET method.

The synthetic resin used in the film making method is preferably a resin excellent in binding properties among the powdery catalyst particles and between the powdery catalyst and the surface of the support, being durable to the reaction environment and not adversely affecting the reaction system. The synthetic resins used include various thermoplastic resins and thermosetting resins, for example the high-molecular compounds mentioned in the above examples of the binder, and are preferably those capable of attaining high-molecular weights through crosslinking reaction of the synthetic resins with a curing agent. Particularly, thermosetting resins such as phenol resin, furan resin and epoxy resin are preferable, and more preferably thermosetting resin undergoing condensation reaction upon curing can be used. When such thermosetting resin is used, the crosslinking density is increased by the curing reaction, whereby the strength of the resulting coating and binding properties are improved and the catalyst coating is made further porous by condensation reaction thereby enabling sufficient utilization of the catalyst activity of the powdery catalyst.

When the film-type catalyst is produced by the film making method, a combination of the powdery catalyst of copper/nickel/ruthenium ternary system and phenol resin can be mentioned as an example of the combination of the powdery catalyst and the synthetic resin.

The compounding ratio of the powdery catalyst to the synthetic resin in the film making method is preferably a ratio of 20 to 80 parts by mass, more preferably 30 to 70 parts by mass, even more preferably 40 to 60 parts by mass of the synthetic resin to 100 parts by mass of the powdery catalyst. By regulating the compounding ratio of the powdery catalyst to the synthetic resin in the range mentioned above, the degree of exposure of the powdery catalyst can be controlled to effectively utilize its catalyst activity, and release of the coating can be prevented. When the amount of the synthetic resin incorporated is 80 parts by mass or less, the thickness of the synthetic resin covering the surface of the powdery catalyst or the degree of coverage with the synthetic resin is made suitable, and the catalyst activity of the powdery catalyst can be sufficiently demonstrated to exhibit a high catalyst activity. When the amount of the synthetic resin incorporated is 20 parts by mass or more, the catalyst activity is sufficiently demonstrated, and the binding strength among the powdery catalyst particles or between the powdery catalyst and the support can be improved to reduce the amount of the catalyst layer released or partially removed during the process of producing the film-type catalyst and during the reaction operation.

In the film making method, a solvent as a third component can be preferably used in order to prepare a coating in addition to the powdery catalyst and the synthetic resin. The solvent may be any solvent which does not adversely affect the reaction activity of the powdery catalyst. Depending on the kind of the synthetic resin used, the solvent can be selected from various kinds of water-soluble solvents or water-insoluble solvents. The pore structure of the film-type catalyst can be controlled by selection of the solvent. Examples of the solvent include water; alcohols such as methyl alcohol, ethyl alcohol, isopropyl alcohol, butyl alcohol and allyl alcohol; glycols and derivatives thereof such as ethylene glycol, propylene glycol, diethylene glycol, polyethylene glycol, polypropylene glycol, diethylene glycol monoethyl ether, polypropylene glycol monoethyl ether, polyethylene glycol monoallyl ether and polypropylene glycol monoallyl ether; glycerol and derivatives thereof such as glycerol, glycerol monoethyl ether and glycerol monoallyl ether; ethers such as tetrahydrofuran and dioxane; ketones such as methyl ethyl ketone, methyl isobutyl ketone and acetone; hydrocarbons such as liquid paraffin, decane, decene, methyl naphthalene, decalin, kerosine, diphenyl methane, toluene, dimethyl benzene, ethyl benzene, diethyl benzene, propyl benzene, cyclohexane and partially hydrogenated triphenyl; silicone oils such as polydimethyl siloxane, partially octyl-substituted polydimethyl siloxane, partially phenyl-substituted polydimethyl siloxane and fluorosilicone oil; halogenated hydrocarbons such as chlorobenzene, dichlorobenzene, bromobenzene, chlorodiphenyl and chlorodiphenyl methane; fluorides such as DAILROL (DAIKIN INDUSTRIES, Ltd.) and DEMNUM (DAIKIN INDUSTRIES, Ltd.); ester compounds such as ethyl benzoate, octyl benzoate, dioctyl phthalate, trioctyl trimellitate, dibutyl sebacate, ethyl (meth)acrylate, butyl (meth)acrylate and dodecyl (meth)acrylate, as well as dimethylformamide, N-methyl-pyrrolidone, acetonitrile and ethyl acetate. The solvent is preferably the one having an excellent ability to solubilize the synthetic resin and may be a mixed solvent of two or more of solvents. By selecting a solvent adapted to the synthetic resin selected, the pore structure can be regulated.

In the film making method, preparation of a coating containing the powdery catalyst and synthetic resin can be carried out in a usual manner, and the coating can be prepared by using selected steps such as a kneading step, a dissolving step, a dispersing step with a sand mill or the like, and a filtering step. In the dispersing step, a paint shaker, a basket mill, a grain mill, DYNO-mill, an agitating mill or the like is used to form the coating.

In preparation of the coating in the film coating method, it is known that by selecting suitable conditions such as dispersing time, the reaction characteristics of the finally obtained film-type catalyst and the strength of the coating (catalyst layer) can be improved and the release of the coating (film-type catalyst layer or powdery catalyst) can be prevented. Particularly, the characteristics can be controlled in connection with the degree of dispersion of the coating. The criteria of the degree of dispersion of the coating can be numerically expressed by means such as glossiness, a grindometer, viscosity and rheological characteristics. In the dispersing step, dispersing treatment can be carried out efficiently when the solids content of the coating is high, and the solids content is preferably 10 to 80 mass %, more preferably 20 to 70 mass %, more preferably 25 to 65 mass %. The viscosity of the coating is preferably 5 to 10,000 mPa·s, more preferably 20 to 5000 mPa·s, even more preferably 50 to 1000 mPa·s. For example, the powdery catalyst, synthetic resin and solvent are added to a stainless steel vat, mixed and stirred until visually recognizable mass of the powdery catalyst disappears, and then the mixture is transferred into a vessel of a basket mill and then mixed and dispersed at a predetermined revolution number and aggregates or foreign matter are removed by precision filtration, whereby the objective coating can be prepared. In the dispersing treatment for preparing the coating, the starting materials when introduced in an amount of 10,000 g (total amount of the powdery catalyst, synthesis resin and solvent) for example into a mixing tank of a 20-L basket mill are stirred desirably at 800 to 3000 rpm for 30 to 600 minutes. The dispersing treatment, when judged with glossiness, is conducted desirably until, for example, evaluated glossiness confirmed with time reaches the maximum. The dispersing treatment, when judged with a grindometer, is conducted desirably until secondary aggregation has been reduced in judgment based on the primary particle diameter of the powdery catalyst.

In preparing the coating by the film making method, the coating can be compounded with a surfactant as a dispersing agent, a coupling agent, inorganic particles and fibrous materials as aggregate, and a high-boiling solvent as an agent for aiding in increasing porosity, in addition to the powdery catalyst, synthetic resin and solvent. The coupling agent has an effect of improving physical properties by molecular crosslinkage in the interface between the inorganic filler and the organic polymer matrix. As the coupling agent, it is possible to use a coupling agent generally known as silane coupling agent, titanate-based coupling agent and aluminate-based coupling agent, and a combination of a plurality of coupling agents can be incorporated and may be used after dilution with a compatible organic solvent for concentration regulation. As the fibrous materials, organic or inorganic fibers are used. The organic fibers include polyamide fibers such as nylon 6 and nylon 66, aramid fiber, polyvinyl alcohol-based fiber, polyester-based polyethylene terephthalate, polybutylene terephthalate fiber, polyarylate fiber, polyvinylidene chloride-based fiber, polyvinyl chloride-based fiber, polyacrylonitrile-based fiber, and polyolefin-based polyethylene and polypropylene fibers. The organic fibers include organic regenerated fibers such as cellulose-based rayon, acetate etc. The inorganic fibers used include glass fiber, carbon fiber, active carbon fiber, ceramic fiber and asbestos, and the mechanical strength of the catalyst coating can be improved by the effect of the aggregate.

The support used in the film making method may be a support made of a durable material not adversely affecting the reaction system in which the film-type catalyst of the present invention is used. The support can be selected suitably depending on the shape of the objective film-type catalyst and can be a planar, tubular, honeycomb or monolithic support.

As the planar support used in the film making method, a support having suitable processability enables shaping of the catalyst formed into a film and can be preferably used. Examples of the planar support include a copper foil, stainless steel foil, aluminum foil etc. The copper foil and stainless steel foil can be preferably used from the viewpoint of processability and corrosion resistance.

The honeycomb or monolithic support used in the film making method includes, but is not limited to, supports containing cordierite, carbon composite, mullite, clay, magnesia, talc, zirconia, spinel, alumina, silica, ceria, titania, tungsten, chrome, stainless steel, copper, aluminum, and nickel. The term "honeycomb" refers to a shape having a large number of assembled cells, forming a bees' nest structure divided with thin walls. The honeycomb structure has a large surface area per unit volume, and is thus preferably used in the support constituting the film-type catalyst. Each cell is preferably in the form of an equilateral triangle, an equilateral pentagon or an equilateral hexagon in which cells can be assembled with no gap, and the support can also be constituted by combining section-shape cells or polygonal cells. For example, an integrally molded structure formed by extrusion molding, or a support formed by stacking, with a flat material, several corrugated layers obtained by shaping flat materials, can also be preferably used as the honeycomb support.

The surface of the support used in the film making method is preferably subjected to roughing treatment or coupling treatment from the viewpoint of improving the adhesion thereof to the catalyst layer. In this coupling treatment, the above-mentioned coupling agent can be used, and preferably the same coupling agent as used in preparing the coating can be used.

Specifically, the film making method includes a method of applying the coating containing the powdery catalyst onto the surface of the support to form a film thereon. This film making method may be a conventional method including various coating methods such as blade coating, roll coating, knife coating, bar coating, spray coating, dip coating, spin coating, comma coating, kiss-roll coating, gravure coating and die coating. The pore structure is regulated at the time of eliminating volatile components such as solvent from the catalyst layer formed as a film, and thus the solids content of the coating in making the film influences formation of the pore structure. The solids content of the coating in forming the film is preferably in the range of 10 to 80 mass %, more preferably 20 to 70 mass %, even more preferably 25 to 65 mass %. The viscosity of the coating in forming the film is selected in a preferable range depending on each of the coating methods mentioned above, and is preferably 5 to 10,000 mPa·s, more preferably 20 to 5000 mPa·s, even more preferably 50 to 1000 mPa·s.

In the film making method by coating, the drying and curing treatment can be carried out after the coating containing the powdery catalyst is applied onto the surface of the support. The drying and curing treatment step is carried out preferably in an atmosphere such as heated air, water vapor, nitrogen or an inert gas such as argon, or by using various means such as a method of spraying such heated medium, a method of utilizing radiation heat with infrared rays or far infrared rays, and a heating system using an induction current by an electromagnetic wave. A combination of these methods or a method of natural drying (air-drying) at ordinary temperatures can also be used. The volatile components eliminated in this step include cured reaction products and unreacted monomer components in addition to the solvent.

The drying conditions in the film making method by coating should be regulated depending on the physical properties of the synthetic resin and volatile components based on the solvent contained in the coating. The pore structure (pore volume) of the film-type catalyst layer can be regulated by selecting a suitable solvent and by setting drying and curing conditions. That is, the pore structure is determined not only at the stage of evaporation of volatile components such as solvent from the coating, but also at the time of formation of a crosslinked structure (network structure) formed by progress of the curing and crosslinking reaction and also at the stage of elimination of condensation products when the reaction is accompanied by condensation reaction. Generally, the components are evaporated more rapidly from the catalyst layer and the pore structure (pore diameter, volume) is increased as the temperature is raised and the air flow is increased in the heating treatment with hot air. The pore structure is decreased as the temperature is reduced and the air flow is decreased.

In the film-forming method by coating, the drying and curing treatment can make use of a method and conditions not adversely affecting the inherent activity of the powdery catalyst, in order to regulate the pore volume in the range of 0.5 to 30 mL/m². With respect to drying and curing conditions with hot air for obtaining the objective film-type catalyst, the drying and curing treatment is carried out desirably at a temperature of typically 50 to 400° C., preferably 70 to 250° C., more preferably 80 to 150° C., at an air flow of preferably 0.5 to 30 m/sec., more preferably 1 to 20 m/sec., for a period of preferably 1 or more seconds, more preferably 10 minutes or more, even more preferably 30 minutes or more.

In the film making method by coating, it is preferable that the coating is dried immediately after application onto the support, wherein the pore structure of the coating can be controlled by regulating the drying conditions. Accordingly, the time of from formation of the catalyst layer on the support to elimination of volatile components such as solvent is desirably shorter, preferably 2 hours or less, more preferably 30 minutes or less.

When thermosetting resin is used as the synthetic resin or the plasticity of the synthetic resin is reduced by crosslinking reaction in the film making method by coating, it is desired that the coating film obtained by coating and drying is subjected to shaping while it remains uncured (prepolymer state), followed by final heating treatment to form the film-type catalyst.

In the film making method involving the final heating treatment, the drying treatment carried out before the final heating treatment is finished while the synthetic resin remains unhardened in part. Desirably, the synthetic resin is partially cured to such a degree that it can be handled at the time of shaping, and the retaining properties and mechanical strength of the catalyst layer are improved as compared with those at the time of coating, and the volatilize components such as solvent may remain in the order of several % in the coating film. Hot-air drying before the final heating treatment for obtaining the objective film-type catalyst is carried out desirably at a temperature of typically 50 to 400° C., preferably 70 to 250° C., more preferably 80 to 150° C., at an air flow of preferably 0.5 to 30 m/sec., more preferably 1 to 20 m/sec., for a period of preferably 0.5 to 300 seconds, more preferably 1 to 100 seconds.

In the film making method involving the final heating treatment, the coating layer is shaped before it is completely cured, whereby the coating layer can follow the shape of the elastically deformed support to improve shaping processability. After the processing is finished, the coating layer can be completely cured by heating treatment thereby fixing the crosslinked structure of the catalyst layer in the final stage of the production process, relieving the residual stress of the catalyst layer and reducing release of the catalyst layer or the powdery catalyst from the film-type catalyst. When thermoplastic resin is contained as the synthetic resin, it is desired that the coating film obtained by coating and drying is subjected to shaping and then to final heating. When thermoplastic resin is contained in the coating film, residual stress may be generated in the coating upon elastic deformation of the support subjected to shaping, thus adversely affecting the retaining properties of the coating film. Accordingly, the stress can be relieved by the final heating treatment, and simultaneously the twisted structure of the thermoplastic resin is reinforced thereby reducing the release of the catalyst layer or the powdery catalyst from the film-type catalyst. The final heating treatment conditions vary depending on the kind of the synthetic resin, but in the present invention, this treatment is carried out desirably at a temperature of preferably 80 to 400° C., more preferably 100 to 200° C., for a period of preferably 5 to 600 minutes, more preferably 10 to 100 minutes.

By the process of the process of the present invention, an alcohol and a primary or secondary amine are used as the starting materials to produce a tertiary amine, whereby the corresponding tertiary amine can be obtained highly sensitively in high yield. Particularly, the cycle consisting of step (i) to step (iii) is repeatedly carried out whereby high productivity can also be achieved.

BRIEF DESCRIPTION OF THE DRAWINGS

In the drawings, reference numerals are below explained.

1, a reaction vessel; 2, 21, condensers; 3, 4, 9, 10, 11, 12, 13, 19, 20, conduits; 5, 6, 7, reaction towers; 8, 18, pumps; 14, 15, gas/liquid separation vessels; 17, a buffer tank.

EXAMPLE

In the following examples, "%" and "parts" refer to "% by mass" and "parts by mass" respectively unless otherwise specified.

Production Example 1

Production of a Powdery Catalyst

Synthetic zeolite was charged into a 1-L flask, and then a solution of copper nitrate, nickel nitrate and ruthenium chloride dissolved in water in a molar ratio of Cu:Ni:Ru=4:1:0.01, and then the solution was heated under stirring. An aqueous solution of 10 wt % $Na_2CO_3$ was added dropwise thereto at 90° C. while the pH of the aqueous solution was controlled in the range of 9 to 10. After aging for 1 hour, the precipitates were filtered, washed with water, dried at 80° C. for 10 hours and calcined at 600° C. for 3 hours to obtain a powdery catalyst.

In the resulting powdery catalyst, the proportion of the metal oxide was 50%, and the proportion of the synthetic zeolite was 50%.

Production Example 2

Production of a Pellet-Type Catalyst

The powder before calcination obtained in the step of preparing the powdery catalyst in Production Example 1 was molded into tablets in a cylindrical form of 3 mmϕ×3 mm and then calcinated at 600° C. for 3 hours to obtain a ternary pellet-type catalyst having copper-nickel-ruthenium supported on synthetic zeolite.

In the resulting pellet-type catalyst, the proportion of the metal oxide was 50%, and the proportion of the synthetic zeolite was 50%.

Production Example 3

Production of a Film-Type Catalyst

Phenol resin (PR-9480 with 58% non-volatiles, manufactured by Sumitomo Bakelite) was added as a binder to 100 parts of the powdery catalyst in Production Example 1 such that the content of non-volatiles in the phenol resin became 47.7 parts. 2-Butanone was added as solvent thereto such that solids content (the powdery catalyst and non-volatiles in the phenol resin) became 55%. The mixture was preliminarily mixed by a Disper for 10 minutes, then mixed and dispersed at 1500 rpm for 70 minutes in a basket mill (SS-3, charged with 1900 g (800 mL) titania beads having a diameter of 1.4 mm, manufactured by ASADA IRON WORKS, Co., Ltd.) to form a coating. A copper foil (thickness 40 μm) was used as a support, and the coating was applied by a bar coater on both sides of the support and dried at 150° C. for 30 seconds. Half of the resulting dried specimen was corrugated in a corrugate form, stacked alternately with the remaining planar catalyst specimens, wound together, and cured at 150° C. for 90 minutes, to fix the film-type catalyst on both sides of the copper foil. The thickness of the resulting film-type catalyst on one side, excluding the thickness of the copper foil, was 4.9 μm, and the amount of the catalyst per unit area was 6.3 g/m².

Example 1

Figure 1:
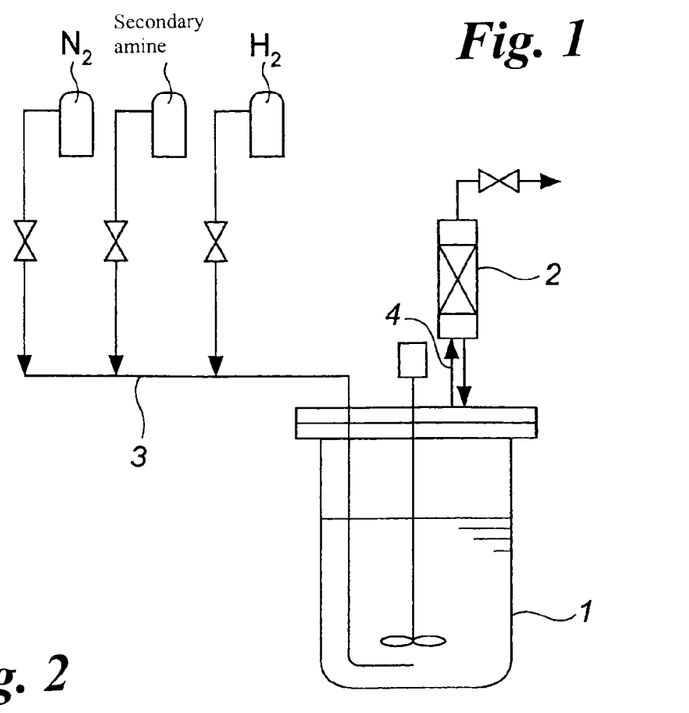
FIG. 1 is a schematic view of the batch reactor used in Example 1.

Using the batch reactor shown in FIG. 1, N-dodecyl-N,N-dimethylamine was produced from lauryl alcohol and dimethylamine as the starting materials.

In FIG. 1, a reaction vessel 1 is a 2-L stirring tank reactor for carrying out step (i) to step (iii). A hydrogen gas and/or a secondary amine (dimethylamine) and/or a nitrogen gas are fed continuously through conduit 3, while an unreacted gas and/or a secondary amine and/or water generated by dehydration reaction of a secondary amine adduct are discharged continuously through conduit 4. The components discharged from the conduit 4 may contain not only those described above but also an alcohol and/or an aldehyde and/or a secondary amine adduct and/or a vapor or mist of formed tertiary amine, and these components are liquefied by condenser 2 and returned to the reaction vessel 1, and the remaining gaseous components are discharged outside of the system.

In this example, 1200 g lauryl alcohol (KALCOL 20 manufactured by Kao Corporation) was introduced as starting alcohol into the reaction vessel 1, and while a nitrogen gas was fed at a flow rate of 15 NL/hr, the temperature in the reaction vessel 1 was kept at 220° C. under stirring at normal pressures. Then, 2.5 g of the powdery catalyst prepared in Production Example 1, after subjected to reduction treatment, was introduced into the reaction vessel 1 and stirred for 4 minutes, and the whole solution was removed and filtered to separate the catalyst. The filtrate was analyzed by gas chromatography and quantified by the area percentage method, and the result indicated that the content of dodecyl aldehyde formed by dehydrogenation of lauryl alcohol was 2.4%.

1000 g of the above filtrate was introduced into the reaction vessel 1 from which the powdery catalyst had been removed by washing, and while a nitrogen gas was fed at a flow rate of 24 NL/hr, the temperature in the reaction vessel 1 was kept at 70° C. under stirring at normal pressures. After supply of a nitrogen gas was finished, dimethylamine was fed at a flow rate of 60 g/hr to the reaction vessel 1 and then left for 70 minutes, and the whole solution in the vessel was removed. The removed whole solution was analyzed by gas chromatography and quantified by the area percentage method, and the result indicated that the total content of 1-(N,N-dimethylamino)-1-dodecanol and 1-(N,N-dimethylamino)-1-dodecene formed by the addition reaction of dodecyl aldehyde with dimethylamine was 2.8%.

820 g of the removed solution was introduced into the reaction vessel 1, and then 40 g of the pellet catalyst prepared in Production Example 2, after subjected to reduction treatment, was introduced into a basket, and an agitating blade of an agitating shaft in the reaction vessel 1 was detached, and this basket was arranged. The atmosphere in the reaction vessel 1 was replaced by a nitrogen gas and then by a hydrogen gas, and while a hydrogen gas was fed at a flow rate of 450 NL/hr, the solution in the reaction vessel 1 was stirred at a pressure of 3.0 MPa and then heated to 140° C. After the solution in the reaction vessel 1 reached 140° C., it was kept for 60 minutes, and then the whole solution in the vessel was removed. The solution was analyzed by gas chromatography and quantified by the area percentage method, and the result indicated that the increased amount of N-dodecyl-N,N-dimethylamine formed by hydrogenation reaction of 1-(N,N-dimethylamino)-1-dodecanol and 1-(N,N-dimethylamino)-1-dodecene was 2.8%, and tertiary amine side products in this case, i.e. N,N-didodecyl-N-methylamine and N,N,N-tridodecylamine, could not be detected.

Example 2

Figure 2:
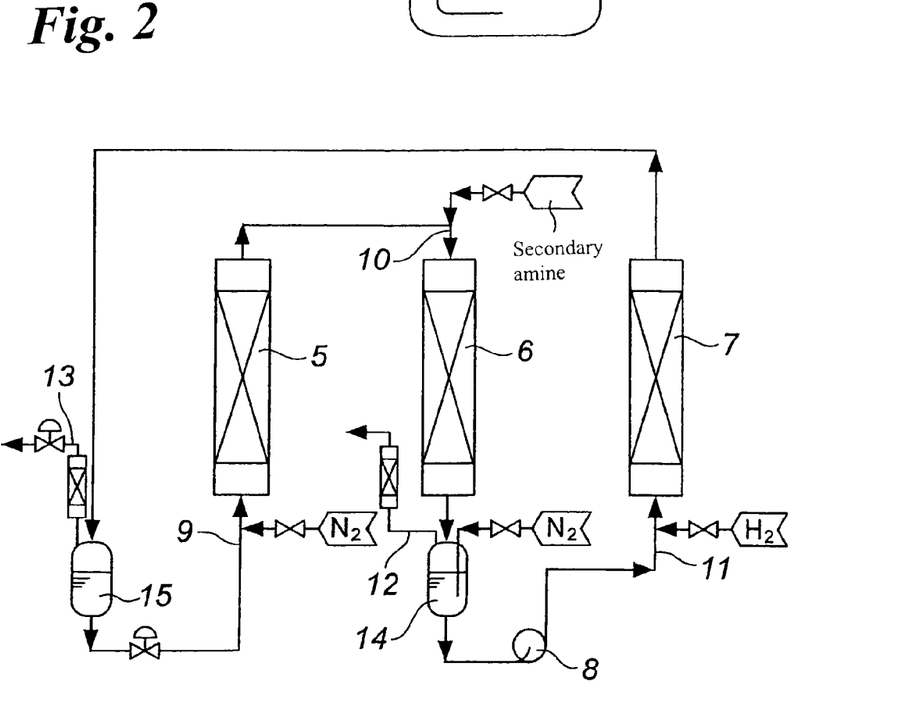
FIG. 2 is a schematic view of the circulating fixed-bed reactor used in Example 2.

Using the circulating fixed-bed reactor shown in FIG. 2, N-dodecyl-N,N-dimethylamine was produced from lauryl alcohol and dimethylamine as the starting materials.

A reaction tower 5 in FIG. 2 is a vertical tubular fixed-bed reactor having an inner diameter of 21.4 mm for carrying out step (i), and was loaded with 140 cc of the film-type catalyst obtained in Production Example 3 as a dehydrogenation catalyst after subjected to reduction treatment. A mixture of the reactants and/or the product, and a nitrogen gas as a nonoxidative atmosphere, are fed continuously through conduit 9 to the bottom of the reactor, while a mixture of the unreacted materials and/or the product, and a nitrogen gas, are recovered continuously from the top of the reactor. A reaction tower 6 is a vertical tubular fixed-bed reactor having an inner diameter of 17.5 mm for carrying out step (ii), and is loaded with 50 cc of Raschig rings (φ5 mm) as an inert packing. A mixture of the product recovered from the reaction tower 5 and/or the product and a nitrogen gas and the secondary amine (dimethylamine) are fed continuously through conduit 10 to the top of a reaction tower 6, while a mixture of the unreacted materials and/or the product, and a nitrogen gas, are recovered continuously from the bottom of the reaction tower 6, followed by gas/liquid separation in vessel 14. The liquid component is recovered through conduit 11, while the gaseous phase is discharged through conduit 12 out of the system. In the vessel 14, the solution is bubbled with a nitrogen gas, whereby the secondary amine (dimethylamine) dissolved in the solution is effectively separated and removed from the liquid component to the gaseous phase. The nitrogen gas and the secondary amine (dimethylamine), similar to the above nitrogen gas, are discharged via conduit 12 out of the system. The pressure in the reaction towers 5 and 6 is kept at almost normal pressures. The reaction tower 7 is a vertical tubular fixed-bed reactor having an inner diameter of 28.4 mm for carrying out step (iii), and is loaded with 250 cc of the same film-type catalyst as in step (i), which was obtained in Production Example 3 as a dehydrogenation catalyst after subjected to reduction treatment. A hydrogen gas and a mixture of the reactants and/or the product recovered via the conduit 11 from the reaction tower 6 were fed by pump 8 continuously through conduit 11 to the bottom of a reaction tower 7 and kept at a pressure of 0.9 MPa. A mixture of the unreacted materials and/or the product, and an unreacted hydrogen gas, are recovered continuously from the top of the reaction tower. The recovered mixture is separated in vessel 15 into a gaseous component and a liquid component, and the gaseous component is discharged via conduit 13 to the outside of the system, and the liquid component is sent through conduit 9 to the reaction tower 5 again and reacted in the circulating system.

In this example, 770 g mixture containing 72.7% N-dodecyl-N,N-dimethylamine and 26.3% lauryl alcohol (KALCOL 20 manufactured by Kao Corporation) as starting alcohol was introduced into vessel 14, then the atmosphere in the vessel 14 was replaced by a nitrogen gas, and the mixture was heated to 60° C. Then, each conduit and the reaction towers 5 to 7 were heated to 60° C., and then the supply of a nitrogen gas into the reaction tower 5 and the supply of a hydrogen gas into the reaction tower 7 were initiated. Then, pump 8 was actuated to initiate supply of the starting alcohol into the reaction tower 7. The starting alcohol was passed through the reaction towers 5 and 6 in this order, and it was confirmed that the starting alcohol recovered in each reaction tower was circulating. Then, the solution in the reaction tower 5 and in the vessel 14 was heated to a temperature of 220° C., and the reaction tower 7 was heated to 160° C., and then dimethylamine was fed to the reaction tower 6 (temperature of which was not controlled) to initiate the reaction. Simultaneously, a nitrogen gas was fed to the solution in the vessel 14 to initiate bubbling.

The flow rate of the circulating solution was 4.0 L/hr, the feed rate of a nitrogen gas into the reaction tower 5 was 70 NL/hr, and the feed rate of a hydrogen gas into the reaction tower 7 was 90 NL/hr. The feed rate of a nitrogen gas into the solution in the vessel 14 was 70 NL/hr.

The sample was collected with time and analyzed with gas chromatography and quantified by the area percentage method, and the solution was circulated and reacted until the unreacted lauryl alcohol as the starting material was reduced to 3.3%. Thereafter, the supply of the gas and liquid was stopped, and the atmosphere was replaced by a nitrogen gas, and the whole solution was removed. The amount of dimethylamine fed was regulated in the range of 12 to 22 g/hr (17 g/hr on average during the reaction) depending on the progress of the reaction. The temperature of the reaction tower 6 was 211 to 215° C. As a result of analysis by gas chromatography, it was revealed that when the increased amount of N-dodecyl-N,N-dimethylamine was 11.0%, the increased amount of the tertiary amine side product N,N-didodecyl-N-methylamine was 0.3%, and the tertiary amine side product N,N,N-tridodecylamine was not detected (that is, no increase thereof). When the increased amount of N-dodecyl-N,N-dimethylamine was 20.9%, the increased amount of the tertiary amine side product N,N-didodecyl-N-methylamine was 1.0%, and the tertiary amine side product N,N,N-tridodecylamine was not detected (that is, no increase thereof).

Comparative Example

Figure 3:
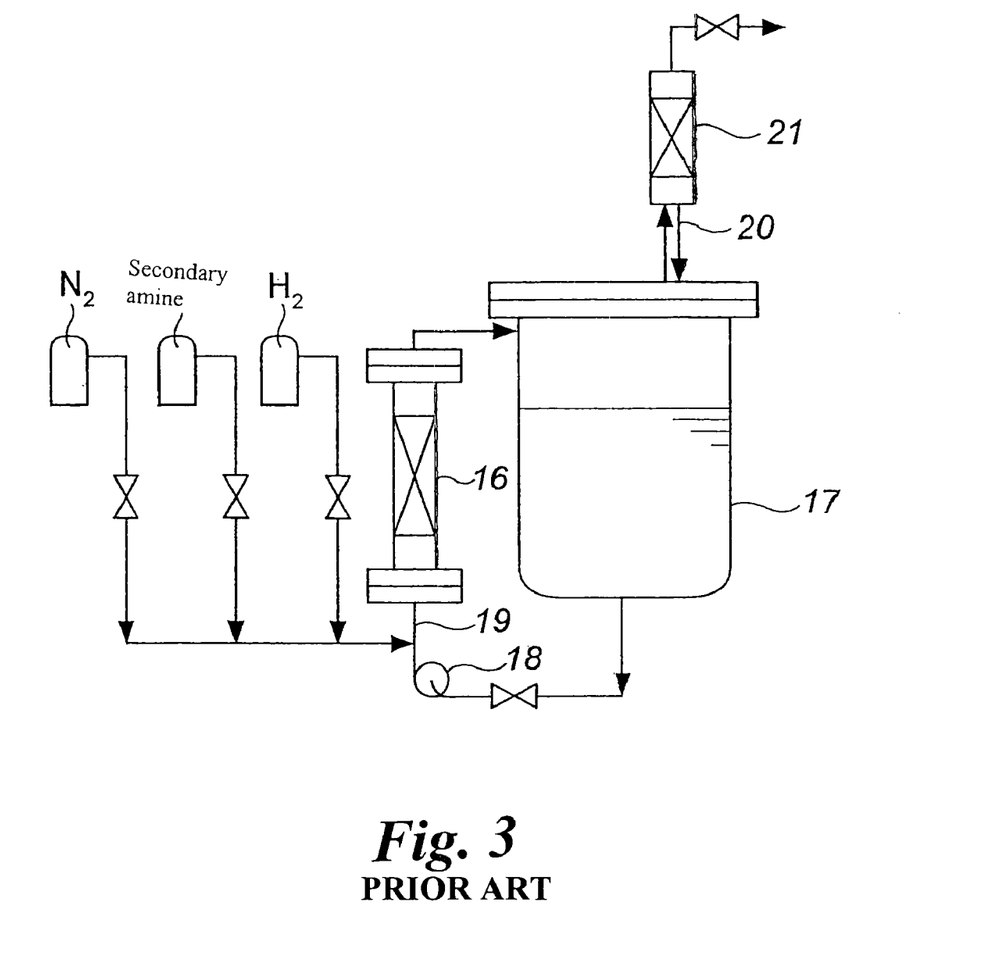
FIG. 3 is a schematic view of the circulating fixed-bed reactor used in Comparative Example.

Using the circulating fixed-bed reactor shown in FIG. 3, N-dodecyl-N,N-dimethylamine was produced from lauryl alcohol and dimethylamine as the starting materials.

The reaction tower 16 in FIG. 3 is a vertical tubular fixed-bed reactor having an inner diameter of 29.5 mm and was loaded with 270 cc of the film-type catalyst obtained in Production Example 3 as a dehydrogenation catalyst after subjected to reduction treatment (there was no catalyst in a buffer tank 17). 1000 g mixture containing 72.0% N-dodecyl-N,N-dimethylamine and 27.0% lauryl alcohol (KALCOL 20 manufactured by Kao Corporation) as starting alcohol was introduced into the buffer tank 17, then the atmosphere in the tank 17 was replaced by a nitrogen gas, and the solution was heated to 60° C. While a hydrogen gas was fed at a flow rate of 20 NL/hr, circulation of the solution was initiated at a flow rate of 7.5 L/hr between the buffer tank 17 and the reaction tower 16.

After the reaction tower 16 was heated to a temperature of 220° C., dimethylamine was fed to the reaction tower 16 to initiate the reaction at 220° C. The sample was collected with time and analyzed by gas chromatography and quantified by the area percentage method, and the solution was reacted under circulation until the unreacted lauryl alcohol as the starting material was reduced to 1.9%. Thereafter, the supply of dimethylamine was stopped, and the atmosphere was replaced by a nitrogen gas, and the whole solution was removed. The amount of dimethylamine fed was regulated in the range of 60 to 110 g/hr (85 g/hr on average during the reaction) depending on the progress of the reaction. As a result of analysis by gas chromatography, it was revealed that when the increased amount of N-dodecyl-N,N-dimethylamine was 10.2%, the increased amount of the tertiary amine side product N,N-didodecyl-N-methylamine was 1.4%, and the tertiary amine side product N,N,N-tridodecylamine was not detected (that is, no increase thereof). When the increased amount of N-dodecyl-N,N-dimethylamine was 17.2%, the increased amount of the tertiary amine side product N,N-didodecyl-N-methylamine was 4.3%, and the tertiary amine side product N,N,N-tridodecylamine was not detected (that is, no increase thereof).

The reaction conditions and the results in Example 2 and Comparative Example are collectively shown in Table 1.

TABLE 1

| | | Example 2 | | Comparative example | |
|---|---|---|---|---|---|
| Step (i) | Kind of catalyst/shape | Cu—Ni—Ru/film type | | Kind of catalyst/shape Cu—Ni—Ru/film type | |
| | Catalyst amount | 140 cc | | Catalyst amount 270 cc | |
| | Reactor | Vertical tublar fixed-bed reactor | | Reactor | |
| | Reaction conditions | | | Vertical tublar fixed-bed reactor | |
| | Temperature | 220° C. | | Reaction conditions | |
| | Pressure | Normal pressure | | Reaction temperature 220° C. | |
| | Fed amount of nitrogen | 70(NL/Hr) | | Reaction pressure Normal pressure | |
| Step (ii) | Catalyst | No catalyst | | Fed amount of hydrogen 20(NL/Hr) | |
| | Reactor | Vertical tublar reactor | | Fed amount of dimethylamine | |
| | Reaction conditions | | | 60~110(g/Hr) | |
| | Tempreture | 211~215° C. | | (85 g/Hr on the average of reaction time) | |
| | Pressure | Normal pressure | | | |
| | Fed amount of dimethylamine | 12~22(g/Hr) | | | |
| | | (17 g/Hr on the average of reaction time) | | | |
| Step (iii) | Kind of catalyst/shape | Cu—Ni—Ru/film type | | | |
| | Catalyst amount | 250 cc | | | |
| | Reactor | Vertical tublar fixed-bed reactor | | | |
| | Reaction conditions | | | | |
| | Temperature | 160° C. | | | |
| | Pressure | 0.9 MPa | | | |
| | Fed amount of hydrogen | 90(NL/Hr) | | | |
| Analysis | | ① | ② | ① | ② |
| results | N-dodecyl-N,N-dimethylamine | Increased amount 11.0% | Increased amount 20.9% | Increased amount 10.2% | Increased amount 17.2% |
| | N,N-didodecyl-N-methylamine | Increased amount 0.3% | Increased amount 1.0% | Increased amount 1.4% | Increased amount 4.3% |
| | N,N,N-tridodecylamine | Not detected | Not detected | Not detected | Not detected |

The invention claimed is:

1. A process for producing a tertiary amine, the process comprises:
   (i) dehydrogenating an alcohol to obtain an aldehyde,
   (ii) reacting the aldehyde with a primary or secondary amine to obtain a primary or secondary amine adduct, and
   (iii) hydrogenating the primary or secondary amine adduct to obtain a tertiary amine,
   wherein (ii) is carried out independently of (i) and (iii).

2. The process according to claim 1, wherein (ii) is carried out in the absence of a catalyst.

3. The process according to claim 1, wherein (i) is carried out in the presence of a dehydrogenation catalyst.

4. The process according to claim 1, wherein (iii) is carried out in the presence of a hydrogenation catalyst.

5. The process according to claim 1, wherein a cycle comprising (i), (ii), and (iii) is repeatedly carried out.

6. The process according to claim 1, wherein (i) is carried out in a reactor comprising a fixed-bed catalyst.

7. The process according to claim 1, wherein (iii) is carried out in a reactor comprising a fixed-bed catalyst.

8. The process according to claim 7, wherein the catalyst in the fixed-bed reactor is in the form of a film.

9. The process according to claim 8, wherein the film has a thickness ranging from 0.1 to 500 gm.

10. The process according to claim 6, wherein the catalyst in the fixed-bed reactor is in the form of a film.

11. The process according to claim 10, wherein the film has a thickness ranging from 0.1 to 500 gm.

12. The process according to claim 1, wherein the alcohol is selected from the group consisting of a linear, saturated $C_8$-$C_{36}$ alcohol, a branched, saturated $C_8$-$C_{36}$ alcohol, a linear, unsaturated $C_8$-$C_{36}$ alcohol, and a branched, saturated $C_8$-$C_{36}$ alcohol.

13. The process according to claim 12, wherein the alcohol is selected from the group consisting of octyl alcohol, lauryl alcohol, myristyl alcohol, stearyl alcohol, behenyl alcohol, and oleyl alcohol.

14. The process according to claim 1, wherein the primary or secondary amine is selected from the group consisting of methylamine, dimethylaime, ethylamine, diethylamine, dodecylamine, and didodecylamine.

15. The process according to claim 1, wherein (i) is conducted at a temperature ranging from 50to 300° C.

16. The process according to claim 1, wherein (ii) is conducted at a temperature of at most 250° C.

17. The process according to claim 1, wherein (iii) is conducted at a temperature ranging from 50to 300° C.

18. The process according to claim 1, wherein the alcohol of (i) is lauryl alcohol and the secondary amine of (ii) is dimethylamine.

19. The process according to claim 18, wherein the tertiary amine is N-dodecyl-N,N-dimethylamine.

* * * * *